United States Patent [19]

Galbo

[11] Patent Number: 5,021,577

[45] Date of Patent: Jun. 4, 1991

[54] POLYSUBSTITUTED N-HYDROCARBYLOXY HINDERED AMINE LIGHT STABILIZERS

[75] Inventor: James P. Galbo, Hartsdale, N.Y.

[73] Assignee: Ciba-Geigy Corporation, Ardsley, N.Y.

[21] Appl. No.: 479,879

[22] Filed: Feb. 14, 1990

Related U.S. Application Data

[63] Continuation-in-part of Ser. No. 326,704, Mar. 21, 1989, abandoned.

[51] Int. Cl.⁵ ................. C07D 401/12; C07D 401/14; C08K 53/435
[52] U.S. Cl. .................................... 546/188; 546/189; 546/190; 546/16; 546/18; 546/19; 546/20; 524/102; 524/103

[58] Field of Search ............... 546/16, 18, 19, 20, 546/188, 189, 190

[56]  References Cited

U.S. PATENT DOCUMENTS

| | | | |
|---|---|---|---|
| 4,191,829 | 3/1980 | Ramey et al. | 524/102 |
| 4,426,472 | 1/1984 | Berner | 524/99 |
| 4,762,872 | 8/1988 | Lai et al. | 524/100 |

OTHER PUBLICATIONS

Derwent 77-86594y/49.
Derwent 89-025378/04.

*Primary Examiner*—Robert T. Bond
*Attorney, Agent, or Firm*—Luther A. R. Hall

[57] ABSTRACT

Polysubstituted N-hydrocarbyloxy hindered amines are effective light stabilizers in protecting organic substrates against the deleterious effects of actinic light.

12 Claims, No Drawings

POLYSUBSTITUTED N-HYDROCARBYLOXY HINDERED AMINE LIGHT STABILIZERS

This is a continuation-in-part of application Ser. No. 326,704, filed on March 21, 1989, now abandoned.

The instant invention pertains to polysubstituted N-hydrocarbyloxy hindered amines and polymer compositions containing said amines which are stabilized against the deleterious effects of actinic light.

BACKGROUND OF THE INVENTION

Monomeric N-hydrocarbyloxy hindered amines are described in copending patent application Ser. No. 259,950.

Copolymers of bis(N-oxylpiperidines) with p-xylylene have been reported in Japanese patent application 79/42000; T. Fujita et al, J. Poly Sci, Poly Chem. Ed, 18, 549 (1980) and 20, 1639 (1982); and J. Poly Sci, Polym Letter Ed, 16, 515 (1978); 17, 353 (1979) and 19, 609 (1981).

The instant polysubstituted N-hydrocarbyloxy derivatives prepared from hindered amines and saturated or unsaturated aliphatic hydrocarbons are not described or suggested in the prior art.

DETAILED DISCLOSURE

The instant invention pertains to polysubstituted N-hydrocarbyloxy compounds of the formula

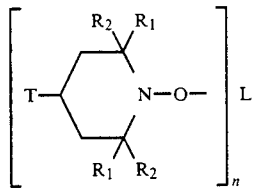

where
n is 2 to 10,
$R_1$ and $R_2$ are independently alkyl of 1 to 4 carbon atoms, or $R_1$ and $R_2$ together are pentamethylene,
L is an n-valent radical of an alkane or alkene of 1 to 18 carbon atoms, an n-valent radical of a cycloalkane or cycloalkene of 5 to 12 carbon atoms, an n-valent radical of a saturated or unsaturated bicyclic or tricyclic hydrocarbon of 7 to 12 carbon atoms or an n-valent radical of an aryl, alkyl substituted aryl or aralkyl hydrocarbon of 6 to 15 carbon atoms, with the proviso that the N—O groups are not necessarily attached to the same carbon atom in L,
T is an organic moiety selected from the group consisting of E—COO—, $E_1$—OCO—, E—CONR$_3$—,

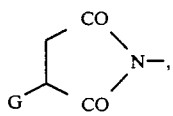

$E_1$NHCOCONH—,

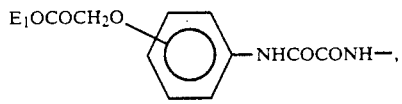

$E_1OCO(CH_2)_mNH—$, $E_1OCO(CH_2)_pCOO—$,

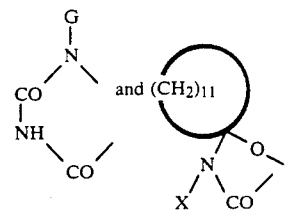

where
E is a radical of an aliphatic, cycloaliphatic, unsaturated aliphatic or aromatic carboxylic acid without the carboxy group,
$E_1$ is a radical of an aliphatic, cycloaliphatic or unsaturated aliphatic alcohol without the hydroxy group, $R_3$ is hydrogen, alkyl of 1 to 8 carbon atoms or

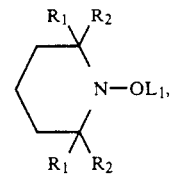

where
$L_1$ is a monovalent radical of the definition of L,
m is 2 to 4, p is 0 to 10,
G is hydrogen or alkyl of 1 to 18 carbon atoms, and
X is hydrogen or —CH$_2$CH$_2$COOC$_{12}$H$_{25}$.
Preferably n is 2 to 4.
Preferably $R_1$ and $R_2$ are each methyl.
Preferably L is an n-valent radical of n-octane, n-heptane or cyclohexane.
Preferably T is E—COO— where E is phenyl, vinyl or alkyl of 1 to 17 carbon atoms, most preferably heptadecyl, or
T is E—CONR$_3$— where $R_3$ is hydrogen and E is vinyl, or
T is

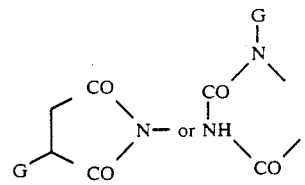

where
G is dodecyl.

SYNTHESIS

Monomeric N-hydrocarbyloxy derivatives of hindered amines, can be made by a variety of synthetic routes. These include:

a. reaction of an N-oxyl compound with an alkyl halide in the presence of tri-n-butyltin hydride (R. L. Kinney et al, J. Am. Chem. Soc. 100, 7902 (1978));

b. reaction of an N-hydroxy compound with an alkyl halide and n-butyllithium or sodium hydride (T. Kurumada et al, J. Poly Sci, Poly Chem. Ed, 22, 277 (1984) and 23, 1477 (1985));

c. The photolysis of a solution of an N-oxyl compound, a hydrocarbon and di-tert-butyl peroxide (D. W. Grattan et al, Polym. Degrad & Stability, 1979, 69);

d. The thermolysis of a solution of an N-oxyl compound, a hydrocarbon and a tert-butyl perester (A. J. Beckwith, J. Org. Chem. 53, 1632 (1988));

e. The photolysis of a solution of an N-oxyl compound, a hydrocarbon and tert-butyl hydroperoxide in an oxygen atmosphere (T. Kurumada et al, J. Polym. Sci, Polym Chem. Ed, 23, 1477 (1985)); and f. The thermolysis of a solution of a hindered amine or an N-oxyl hindered amine, a hydrocarbon, tert-butyl hydroperoxide and a metal oxide catalyst (in copending patent applications Ser. Nos. 259,946 and 259,950).

The instant oligomeric compounds can be prepared by modifications of the methods set forth supra for preparing monomeric N-hydrocarbyloxy compounds.

One convenient method involves the reaction of a (N-oxyl) or (N-hydroxy) hindered amine with a polyhaloalkane.

Most conveniently the instant polysubstituted compounds are prepared by coupling a (N-oxyl) hindered amine with a hydrocarbon n-valent radical generated from the decomposition of a peroxide or hydroperoxide in the presence of a hydrocarbon having abstractable hydrogen atoms.

The ratio of (N-oxyl)hindered amine to hydrocarbon can be adjusted to favor the formation of monomeric N-hydrocarbyloxy compounds or the formation of the instant polysubstituted N-hydrocarbyloxy compounds, but mixtures of monomeric and polysubstituted N-hydrocarbyloxy compounds are nearly always obtained. These mixtures can be easily separated into monomeric and polysubstituted N-hydrocarbyloxy compounds by column chromatography.

When a (N-oxyl) or (N-hydroxy) hindered amine is reacted with a polyhaloalkane, instant compounds of discrete structures are obtained.

Thus, the group L can be assigned a specific structure when the instant compounds are made using the latter method, but the group L represents an isomeric mixture of structures when the instant compounds are made using an N-oxyl compound and a hydrocarbon with hydroperoxide or peroxide.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

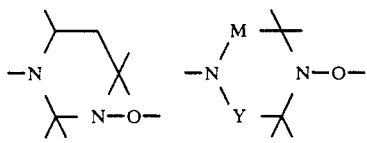

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/ isobutylene, ethylene/butene-1, propylene/butadiene, isobutylene/isoprene, ethylene/alkyl acrylates, ethylene/ alkyl methacrylates, ethylene/vinyl acetate or ethylene/ acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile./methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/ propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/ vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example
2,2'-thio-bis-(6-tert-butyl-4-methylphenol)

2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3,-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid di-octadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tertbutylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1 Par 2, on pages 735 and 742 (Berlin 1972), "Lackkunstharze" (1977), by H. Wagner and H. F. Sarx, on pages 229–238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/ melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are reference in a paper by H. J. Heller in European Polymer Journal Supplement, 1969, pp 105–132. These classes include the phenyl salicylates, the o-hydroxybenzopheones, the hydroxyxanthones, the benzoxazoles, the benzimidazoles, the oxadizaoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tertbutyl-, 4'-octoxy-, and 3',5'-di-tert-amyl derivatives.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyano-β,β-diphenylacrylic acid ethyl ester, or isoctyl ester, alpha-carbomethoxy-cinnamic acid methyl ester, alpha-cyano-β-methyl-p-methoxy-cinnamic acid methyl ester or butyl ester, alphacarbomethoxy-p-methoxy-cinnamic acid methyl ester, N-(β-carbomethoxy-β-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyl-oxanilide and its mixture with 2-ethoxy-2'-ethyl-5,4'-di-tert-butyloxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl)-4-(2-hydroxy-4 octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa-(ethyleneoxy)carbonyl)-ethylphenyl]-2H-benzotriazole, dodecylated 2-(2-hydroxy-5-methylphenyl)-2H-benzotriazole, 2-[2-hydroxy-3-tert.butyl-5-(2-octyloxycarbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alpha-dimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert.butyl-5-(2-octyloxycarbonyl)ethylphenyl]-2H-benzotriazole.

It is also contemplated that the instant compounds will be particularly effective as stabilizers for polyolefin fibers, especially polypropylene fibers, when A preferred embodiment of the instant invention pertains to stabilized compositions comprising (a) an acid catalyzed thermoset coating or enamel based on hot crosslinkable acrylic, polyester or alkyd resins, (b) a NO-L-substituted 2,2,6,6-tetraalkylpiperidine compound, and (c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, diisodecylpentaerythritol diphosphite, di-(2,4-ditert.butylphenyl)pentaerythritol diphosphite, tristearylsorbitol triphosphite, tetrakis-(2,4di-tert.butylphenyl)-4,4'-diphenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

Still another preferred combination of the instant stabilizers is with a hydroxylamine in order to protect polypropylene fibers from gas fading.

The following examples are presented for the purpose of illustration only and are not to be construed to limit the nature or scope of the instant invention in any manner whatsoever.

EXAMPLE 1A

4-Benzoyloxy-1-(2-cyclohexen-1-yloxy)-2,2,6,6-tetramethylpiperidine

A solution of 33.6 grams (122 mmol) of 4-benzoyloxy-1-oxyl-2,2,6,6-tetramethylpiperidine, 23.0 grams (157 mmol) of di-tert-butyl peroxide, and 70 ml of cyclohexene is heated in a Fischer-Porter pressure bottle at 138° C. for 6.5 hours. The reaction mixture is purified by flash chromatography on silica gel (200:1 heptane:ethyl acetate) to afford 35.1 grams (81% yield) of the title compound as a colorless oil.

Analysis: Calcd for $C_{22}H_{31}NO_3$: C, 73.9; H, 8.7; N, 3.9. Found: C, 73.7; H, 8.8; N, 3.9.

EXAMPLE 1B 1,4-Bis(4-benzoyloxy-2,2,6,6-tetramethylpiperidin-1-yloxy)-2-cyclohexene A mixture of 43.6 grams (122 mmol) of the compound prepared in Example 1A, 40.5 grams (147 mmol) of 4-benzoyloxy-1-oxyl-2,2,6,6-tetramethylpiperidine, 17.8 grams (122 mmol) of di-tert-butyl peroxide and 50 ml of 1,2-dichlorobenzene is heated at 135° C. for 5.5 hours in a Fisher-Porter pressure bottle. Fresh di-tert-butyl peroxide (8.0 grams, 55 mmol) is added and the reaction mixture is heated at 135° C. for an additional three hours. The crude reaction mixture is purified by flash chromatography on silica gel (hexane; then 100:3 heptane:ethyl acetate) to afford 4.0 grams of the title compound as a while solid melting at 140°–142° C.

Analysis: Calcd for $C_{38}H_{52}N_2O_6$: C, 72.1; H, 8.3; N, 4.4. Found: C, 72.0; H, 8.5; N, 4.3.

EXAMPLE 2

1,4-Bis(4-benzoyloxy-2,2,6,6-tetramethylpiperidin-1-yloxy)-cyclohexane

The title compound is prepared by the catalytic hydrogenation of 1,4-bis(4-benzoyloxy-2,2,6,6-tetramethylpiperidin-1-yloxy)-2-cyclohexane prepared in Example 1B.

EXAMPLE 3

Bis(4-benzoyloxy-2,2,6,6-tetramethylpiperidin-1-yloxy)octane

A mixture of 55.3 grams (0.2 mol) of 4-benzoyloxy-2,2,6,6-tetramethylpiperidine, 2.8 grams of molybdenum trioxide and 250 ml of n-octane is heated to 120° C. A solution of 90.2 grams (0.7 mol) of 70% aqueous tert-butyl hydroperoxide is added dropwise to the hot reaction mixture. Water is removed by azeotropic distillation and collected in a Dean-Stark trap. The reaction mixture is heated at reflux till the red color of the intermediate N-oxyl compound disappears. Solids are removed by filtration, and the filtrate is concentrated under vacuum to give an oil. Purification of the oil by flash chromatography on silica gel (100:3 heptane: ethyl acetate) affords 4-benzoyloxy-1-octyloxy-2,2,6,6-tetramethylpiperidine as a mixture of octyloxy isomers. Further elution of the chromatographic column with 50:3 heptane:ethyl acetate affords the title compound as a mixture of octanediyl isomers.

EXAMPLE 4

Bis(4-hydroxy-2,2,6,6-tetramethylpiperidin-1-yloxy)octane

The title compound is prepared by basic hydrolysis (potassium hydroxide in ethanol) of the compound prepared in Example 3.

EXAMPLE 5

1,8-Bis(4-benzoyloxy-2,2,6,6-tetramethylpiperidin-1-yloxy)octane

This reaction is carried out under a nitrogen atmosphere. Tributyltin hydride (32.1 grams, 110 mmol) is added dropwise over a three-hour interval to a solution of 66.5 grams (241 mmol) of 4-benzoyloxy-1-oxyl-2,2,6,6-tetramethylpiperidine, 20.1 grams (54.9 mmol) of 1,8-diiodooctane and 160 ml of chlorobenzene. The solution is precooled to 10° C. before addition of the tributyltin hydride begins. The reaction mixture is kept below 20° C. throughout the addition, and is then stirred at room temperature for 17 hours. The red reaction mixture is passed through a column of silica gel (heptane, then 100:3 heptane:ethyl acetate). Fractions containing the desired product are concentrated to give 26.5 grams of a crude solid. Tributyltin iodide is removed by washing a solution of the crude solid with aqueous ammonia. Final purification by flash chromatography (20:1 heptane:ethyl acetate) affords 10.6 grams of the title compound as a white solid melting at 106°–108° C. In contrast to the compound prepared in Example 3, the title compound consists of only one octanediyl isomer. Analysis: Calcd for $C_{40}H_{60}N_2O_6$: C, 72.3; H, 9.1: N, 4.2. Found: C, 72.4; H, 9.4; N, 4.0.

EXAMPLE 6A

Bis(4-benzoyloxy-2,2,6,6-tetramethylpiperidin-1-yloxy)heptane.

The title compound, which consists of a mixture of heptanediyl isomers, is prepared according to the procedure of Example 3 by substitution of heptane for octane.

EXAMPLE 6B

Bis(4-hydroxy-2,2,6,6-tetramethylpiperidin-1-yloxy)-heptane

The title compound is prepared by basic hydrolysis (potassium hydroxide in ethanol) of the compound prepared in Example 6A.

EXAMPLE 7A

Bis(4-benzoyloxy-2,2,6,6-tetramethylpiperidin-1-yloxy)cyclohexane

The title compound, which consists of a mixture of cyclohexanediyl isomers, is prepared according to the procedure of Example 3 by substituting cyclohexane for octane.

EXAMPLE 7B

Bis(4-hydroxy-2,2,6,6-tetramethylpiperidin-1-yloxy)cyclohexane

The title compound is prepared by basic hydrolysis (potassium hydroxide in ethanol) of the compound prepared in Example 7A.

EXAMPLE 8

Bis[4-(3-dodecylsuccinimid-1-yl)-2,2,6,6-tetramethylpiperidin-1-yloxy]octane

The title compound, which consists of a mixture of octanediyl isomers, is prepared according to the procedure of Example 3 by substituting 4-(3-dodecylsuccinimid-1-yl)-2,2,6,6-tetramethylpiperidine for 4-benzoyloxy-2,2,6,6-tetramethylpiperidine.

EXAMPLE 9

Octanediylbis[N-[2-(ethoxycarbonylmethoxy)phenyl]-N'-(1-oxy-2,2,6,6-tetramethylpiperidin-4-yl)oxamide]

The title compound, which is a mixture of octanediyl isomers, is prepared according to the procedure of Example 3 by substituting N-[2-(ethoxycarbonylmethoxy)-phenyl]-N'-(2,2,6,6-tetramethylpiperidin-4-yl)oxamide for 4-benzoyloxy-2,2,6,6-tetramethylpiperidine.

EXAMPLE 10A

Bis(4-acetamido-2,2,6,6-tetramethylpiperidin-1-yloxy)octane

The title compound, which consists of a mixture of octanediyl isomers, is prepared by substituting 4-acetamido-2,2,6,6-tetramethylpiperidine for 4-benzoyloxy-2,2,6,6-tetramethylpiperidine in the procedure according to Example 3.

EXAMPLE 10B

Bis(4-amino-2,2,6,6-tetramethylpiperidin-1-yloxy)octane

The title compound is prepared by the acidic hydrolysis (3N hydrochloric acid at reflux) of the compound prepared in Example 10A.

EXAMPLE 11

Octanediylbis(methyl 1-oxy-2,2,6,6-tetramethylpiperidin-4-yl sebacate)

The title compound, which consists of a mixture of octanediyl isomers, is prepared by substituting methyl 2,2,6,6-tetramethylpiperidin-4-yl sebacate for 4-benzoyloxy-2,2,6,6-tetramethylpiperidine in the procedure according to Example 3.

EXAMPLE 12

Mixture of Bis- and Tris-(4-benzoyloxy-2,2,6,6-tetramethylpiperidin-1-yloxy)octadecane A mixture of 80 mmol of 4-benzoyloxy-1-oxyl-2,2,6,6-tetramethylpiperidine, 250 mmol of 90% tert-butyl hydroperoxide, 125 grams of octadecane and 5 mmol of molybdenum trioxide is heated at 140° C. in a Fischer-Porter prerssure bottle till the red color of the N-oxyl compound is no longer visible. The reaction mixture is purified by flash chromatography.

EXAMPLE 13

1,4-Bis(4-benzoyloxy-2,2,6,6-tetramethylpiperidin-1-yloxy)-1,2,3,4-tetrahydronaphthalene A mixture of 80 mmol of 4-benzoyloxy-1-oxyl-2,2,6,6-tetramethylpiperidine, 300 mmol of 90% tert-butyl hydroperoxide, 5 mmol of molybdenum trioxide and 80 ml of 1,2,3,4-tetrahydronaphthalene (tetralin) is heated at 135° C. in a Fischer-Porter pressure bottle till the red color of the N-oxyl starting material is no longer visible. Purification of the crude reaction mixture by flash chromatography affords the title compound.

EXAMPLE 14

1,4-Bis(4-octadecanoyloxy-2,2,6,6-tetramethylpiperidin-1-yloxy)butane

The title compound is prepared by reaction of a tetrahydrofuran solution of 1-hydroxy-4-octadecanoyloxy-2,2,6,6-tetramethylpiperidine with sodium hydride followed by reaction with 0.5 molar equivalent of 1,4-dibromobutane.

EXAMPLE 15

1,10-Bis(4-benzyloxy-2,2,6,6-tetramethylpiperidin-1-yloxy)decane

The title compound is prepared from 4-benzyloxy-1-oxyl-2,2,6,6-tetramethylpiperidine and 1,10-diiododecane according to the procedure of Example 5.

EXAMPLE 16

(4-benzoyloxy-2,2,6,6-tetramethylpiperidin-1-yloxy)methane

The reaction is carried out in a nitrogen atmosphere. Tributyltin hydride (20.0 grams, 68.7 mmol) is added dropwise over 2.75 hours to a solution, precooled to 10°

C., of 40.0 grams (145 mmol) of 4-benzoyloxy-1-oxyl-2,2,6,6-tetramethylpiperidine, 9.0 grams (33.6 mmol) of methylene iodide (diiodomethane) and 75 ml of chlorobenzene. The reaction temperature reaches 27° C. during the addition. The red mixture is stirred at room temperature for 27 hours after the addition is complete. The reaction mixture is then passed through a column of silica gel (heptane, then 100:3 heptane:ethyl acetate). Fractions containing the desired product are concentrated to give a crude solid. Tributyltin iodide is removed by washing a solution of the crude solid with aqueous ammonia. Final purification by flash chromatography on silica gel (100:3 heptane:ethyl acetate) followed by recrystallization from heptane affords 4.8 grams of the title compound as a white solid melting at 126°–127° C.

Analysis: Calcd for $C_{33}H_{46}N_2O_6$: C, 69.9; H, 8.2; N, 4.9. Found: C, 70.0; H, 8.2; N, 5.0.

EXAMPLE 17A

Bis(4-acetamido-2,2,6,6-tetramethylpiperidin-1-yloxy)-cyclooctane

The title compound, which consists of a mixture of cyclooctanediyl isomers, is prepared from 4-acetamido-2,2,6,6-tetramethylpiperidine and cyclooctane according to the procedure of Example 10A.

EXAMPLE 17B

Bis(4-amino-2,2,6,6-tetramethylpiperidin-1-yloxy)cyclooctane

The title compound is prepared by the hydrolysis in 3N hydrochloric acid at reflux of the compound prepared in Example 17A.

EXAMPLE 18

Mixture of Bis- and Tris(4-benzoyloxy-2,2,6,6-tetramethylpiperidin-1-yloxy)-decahydronaphthalene The title mixture is prepared according to the procedure of Example 12 by substituting decahydronaphthalene (decalin) for octadecane.

EXAMPLE 19

Bis(4-benzoyloxy-2,2,6,6-tetramethylpiperidin-1-yloxy)methylcyclohexane

The title compound, which consists of a mixture of methylcyclohexanediyl isomers, is prepared from 4-benzoyloxy-1-oxyl-2,2,6,6-tetramethylpiperidine and methylcyclohexane according to the procedure of Example 3.

EXAMPLE 20

Bis(4-acryloyloxy-2,2,6,6-tetramethylpiperidin-1-yloxy)octane

The title compound is prepared by the reaction of the compound prepared in Example 4 with acryloyl chloride.

EXAMPLE 21

2,2-Bis(4-benzoyloxy-2,2,6,6-tetramethylpiperidin-1-oxy)propane

The title compound is prepared from 4-benzoyloxy-1-oxyl-2,2,6,6-tetramethylpiperidine and 2,2-dibromopropane according to the procedure of Example 16.

EXAMPLE 22

Light Stabilization of Polypropylene

This example illustrates the light stabilizing effectiveness of instant stabilizers.

Unstabilized polypropylene powder (Himont Profax 6501) is throughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 220° C. and 175 psi ($1.2 \times 10^6$ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

The instant polysubstituted compounds are effective as light stabilizers for protecting polypropylene from the deleterious effects of actinic light.

EXAMPLE 23

Stabilization of High Solids Thermoset Acrylic Resin Enamel

A thermoset acrylic enamel based on a binder of 70% by weight of 2-hydroxyethyl acrylate, butyl acrylate, methyl methacrylate, styrene and acrylic acid and of 30% by weight of a melamine resin in the presence of an acid catalyst, p-toluenesulfonic acid, dinonylnaphthalene disulfonic acid or dodecylbenzenesulfonic acid, is formulated to include 2% by weight based on the resin solids of a benzotriazole ultraviolet absorber and an effective stabilizing amount of the test hindered amine light stabilizer.

Commercially available epoxy primed 4" × 12" (10.16 cm × 30.48 cm) panels (Uniprime from Advanced Coatings Technology) are spray coated with a silver metallic basecoat to a thickness of about 0.8 mil (0.023 mm) and air dried for 3 minutes. The stabilized thermoset acrylic resin enamel is then sprayed onto the basecoated panel to a thickness of about 1.7 mil (0.049 mm). After 15 minutes air-drying, the coated sheets are baked for 30 minutes at 250° F. (121° C.).

After storage for 1 week in a air-conditioned room, the coated panels are subjected to weathering in a QUV exposure apparatus according to test method ASTM G-53/77. In this test, the samples are subjected to weathering in repeated cycles for 4 hours in a humid atmosphere at 50° C. and then for 8 hours under UV light at 70° C. The panels are exposed in the QUV for 1500 hours. The 20° gloss values of the panels are determined before and after exposure.

The loss of gloss of the stabilized panels is considerably less than that of the unstabilized control panels.

What is claimed is:

1. A polysubstituted N-hydrocarbyloxy compound of the formula

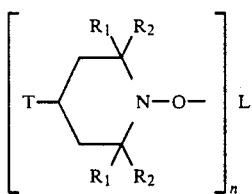

where
n is 2 to 10,
$R_1$ and $R_2$ are independently alkyl of 1 to 4 carbon atoms, or $R_1$ and $R_2$ together are pentamethylene,
L is an n-valent radical of an alkane or alkene of 1 to 18 carbon atoms, an n-valent radical of a cycloalkane or cycloalkene of 5 to 12 carbon atoms, an n-valent radical of a bicyclic or tricyclic hydrocarbon of 7 to 12 carbon atoms or an n-valent radical of an aryl, alkyl substituted aryl or aralkyl hydrocarbon of 6 to 15 carbon atoms, with the proviso that the N—O groups are not necessarily attached to the same carbon atom in L,
T is an organic moiety selected from the group consisting of E—COO—, $E_1$—OCO—, E—CONR$_3$—

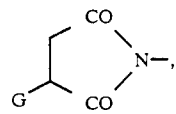

$E_1$NHCOCONH—,

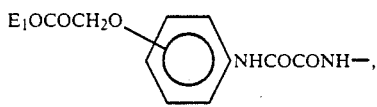

$E_1$OCO(CH$_2$)$_m$NH—, $E_1$OCO(CH$_2$)pCOO—,

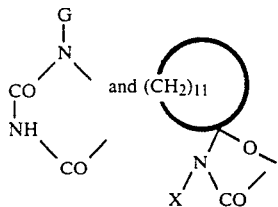

where
E is phenyl, vinyl or alkyl of 1 to 17 carbon atoms,
$E_1$ is methyl or ethyl,
$R_3$ is hydrogen, alkyl of 1 to 8 carbon atoms or

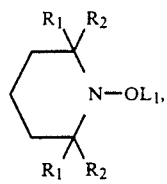

where
$L_1$ is a monovalent radical of the definition of L,
m is 2 to 4, p is 0 to 10,
G is hydrogen or alkyl of 1 to 18 carbon atoms, and
X is hydrogen or —CH$_2$CH$_2$COOC$_{12}$H$_{25}$.

2. A compound according to claim 1 wherein n is 2 to 4.

3. A compound according to claim 1 wherein $R_1$ and $R_2$ are each methyl.

4. A compound according to claim 1 wherein L is an n-valent radical of n-octane, n-heptane or cyclohexane.

5. A compound according to claim 1 wherein T is E—COO— where E is phenyl, vinyl or alkyl of 1 to 17 carbon atoms.

6. A compound according to claim 5 wherein E is heptadecyl.

7. A compound according to claim 1 wherein T is E—CONR$_3$— where $R_3$ is hydrogen and E is vinyl.

8. A compound according to claim 1 wherein T is

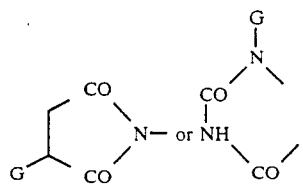

where G is dodecyl.

9. The compound according to claim 1 which is 1,4-bis(4-benzoyloxy-2,2,6,6-tetramethylpiperidin-1-yloxy)-2-cyclohexene.

10. The compound according to claim 1 which is 1,8-bis-(4-benzoyloxy-2,2,6,6-tetramethylpiperidine-1-yl-oxy)octane.

11. The compound according to claim 1 which is bis-(4-benzoyloxy-2,2,6,6-tetramethylpiperidin-1-yloxy)octane.

12. The compound according to claim 1 which is bis-(4-benzoyloxy-2,2,6,6-tetramethylpiperidin-1-yloxy)methane.

* * * * *